(12) United States Patent
van Muiden

(10) Patent No.: US 6,355,013 B1
(45) Date of Patent: Mar. 12, 2002

(54) BALLOON CATHETER WITH LONGITUDINAL SAFETY STOP

(75) Inventor: Johannes Gerardus Maria van Muiden, AZ Peize (NL)

(73) Assignee: Cordis Europe N.V. (NL)

( * ) Notice: Subject to any disclaimer, the term of this patent is extended or adjusted under 35 U.S.C. 154(b) by 0 days.

(21) Appl. No.: 09/594,854

(22) Filed: Jun. 15, 2000

(30) Foreign Application Priority Data

Jul. 6, 1999 (NL) .............................................. 1012527

(51) Int. Cl.[7] .............................................. A61M 29/00
(52) U.S. Cl. .............................. 604/96.01; 604/164.05; 604/915; 606/192
(58) Field of Search .............................. 604/96.01, 103, 604/103.04, 103.06, 103.08–103.09, 103.13–103.14, 915, 921, 164.05, 160–161; 606/192, 194–195

(56) References Cited

U.S. PATENT DOCUMENTS

| | | | |
|---|---|---|---|
| 4,738,666 A | * | 4/1988 | Fuqua |
| 4,796,629 A | | 1/1989 | Grayzel |
| 5,195,978 A | * | 3/1993 | Schiffer |
| 5,318,261 A | | 6/1994 | Davey |
| 5,324,261 A | | 6/1994 | Amundson et al. |
| 5,370,614 A | | 12/1994 | Amundson et al. |
| 5,391,148 A | | 2/1995 | Bonis |
| 5,395,335 A | * | 3/1995 | Jang |
| 5,644,798 A | | 7/1997 | Shah |

FOREIGN PATENT DOCUMENTS

EP 0 737 488 A1 10/1996

* cited by examiner

Primary Examiner—Richard K Seidel
Assistant Examiner—LoAn H. Thanh
(74) Attorney, Agent, or Firm—Michael W. Montgomery

(57) ABSTRACT

The present invention relates to a balloon catheter having a tubular basic body with distal and proximal ends, and at least one lumen extending between the proximal and the distal ends. A balloon is attached to the basic body close to the distal end which is connected with the lumen, so that the balloon may be selectively expanded by means of supplying a medium under pressure through the lumen. The balloon has at least one safety stop, which may extend between the distal and the proximal end of the balloon.

8 Claims, 5 Drawing Sheets

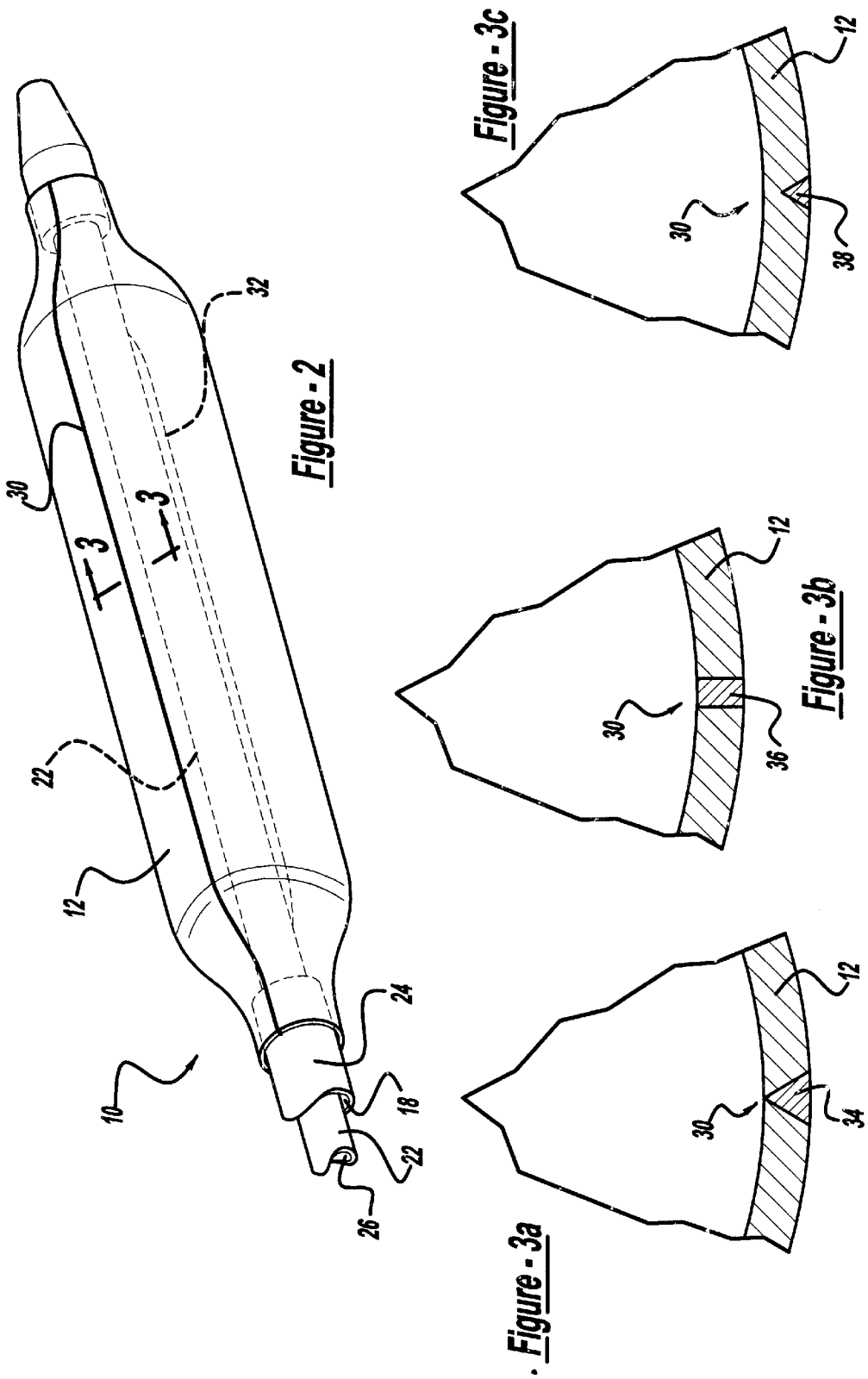

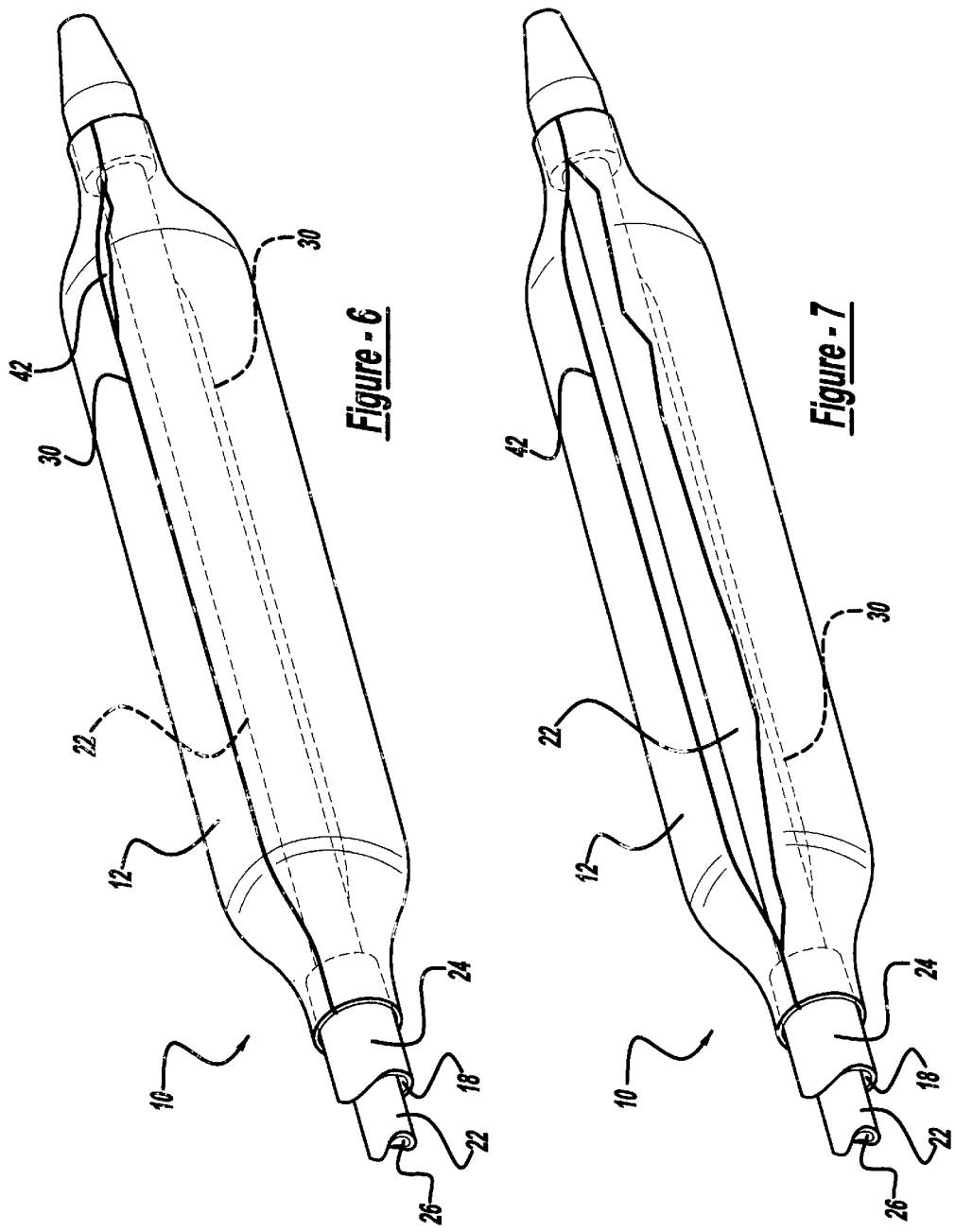

BALLOON CATHETER WITH LONGITUDINAL SAFETY STOP

BACKGROUND AND SUMMARY OF THE INVENTION

1. Technical Background

The present invention relates generally to medical devices, and more particularly to a balloon catheter having an improved tip design.

2. Discussion

Balloon catheters are used in a variety of therapeutic applications, including many vascular treatments such as angioplasty. Angioplasty can be used to treat vascular disease, in which blood vessels may be partially or totally blocked or narrowed by a lesion or stenosis. In many instances of vascular disease, a local area of a blood vessel may become narrowed. This narrowing is called a lesion or stenosis, and may take to form of hard plaque, cholesterol, fats, or viscous thrombus. Such a stenosis may cause heart attack or stroke, which are significant health problems affecting millions of people each year.

During angioplasty, an expansive force may be applied to the lumen of the stenosis. This outward pressing of a constriction or narrowing at the desired site in a body passage is intended to partially or completely reopen or dilate that body passageway or lumen, increasing its inner diameter or cross-sectional area, to encourage greater blood flow through the newly expanded vessel.

As an example, the present invention will be described in relation to coronary, peripheral, and neurovascular angioplasty. However, it should be understood that the present invention relates to any angioplasty catheter having the features of the present invention, and is not limited to catheters for a particular therapeutic procedure.

Some balloon catheters have a relatively long and flexible tubular shaft defining one or more passages or lumens, extending between a hub at a proximal end to a distal end where the balloon is located. The catheter shaft may define an inflation lumen for conducting inflation fluid from an inflation port defined by the proximal hub to selectively inflate or a deflate the balloon, and may define a guidewire lumen extending from a distal guidewire port at the distal end of the catheter to a proximal port located at a position proximal from the balloon.

Among other things, the present invention relates to a balloon catheter having a tubular basic body with a distal end, a proximal end, and at least one inflation lumen extending between the proximal and the distal end, and a balloon close to the distal end which is connected with the inflation lumen, so that the balloon may be selectively expanded or by means of supplying an inflation medium under pressure through the inflation lumen.

Balloon catheters may be used for dilating a blood vessel in which a narrowing or stenosis has formed, or for delivering and deploying a stent, which is a tubular scaffold.

One consideration present in prior balloon catheters is to provide for maximum safety, even in the unlikely event of a balloon burst. The balloon is designed to withstand large inflation pressures, often as much as 12 atmospheres or more. Indeed, the rated burst pressure may often include an additional safety margin.

If a balloon does in fact burst or become punctured by a sharp edge on a stent or calcified lesion within a patient, it is desirable to further enhance the safety feature of the catheter. One possibility is that removal of some prior balloon catheters may be impeded when the balloon is torn. This challenge may be caused by remainders of the balloon attached to the balloon catheter, which may get caught on the guiding catheter introduction system, or may form a bulge such that the balloon may be difficult to pass through the guiding catheter. In rare occasions, the balloon may develop a "radial tear" around the balloon in a radial direction.

Tearing of the balloon may for instance be caused by sharp protrusions on a stent or a stenosis which has calcified and developed sufficiently sharp points to cause perforation of the balloon. It is also a remote possibility that the balloon of some prior balloon catheters may burst due to excessive pressure.

A possible object of the present invention is to provide a balloon catheter having additional safety features. To this end, a balloon catheter may be provided at least one longitudinal safety stop, which extends between the distal and the proximal ends of the balloon.

With a balloon catheter according the present invention, the desired additional safety features have been provided. The balloon preferably has a longitudinal structural feature for encouraging any balloon burst that may occur in rare instances to follow a generally longitudinal pattern, rather than a radial or transverse pattern.

In other words, the longitudinal safety stop of the present invention is intended to cause any possible tear in the balloon material to move toward the longitudinal safety stop and to follow it. One intended result of the present invention is that all of the balloon material remains connected to both the distal and the proximal ends of the balloon, and therefore also connected to the catheter shaft at both ends. Accordingly, it is more likely that all of the balloon material, even after any balloon burst, will remain attached to the catheter shaft up to removal from the patient through any guiding catheter or other delivery system that may have been used.

The present invention also provides a balloon catheter which minimizes any possibility that pieces of balloon material may detach from the balloon catheter.

In order to further enhance the safety features of the present invention, an alternative embodiment would be to include two or more longitudinal safety stops in the balloon material, which are preferably distributed evenly over the balloon.

Within the scope of the present invention different options are possible, such as a longitudinal safety stop extending in the longitudinal direction of the balloon catheter, or a safety stop extending in a helical pattern over the balloon in expanded state.

The present invention also encompasses an elongated element, such as a wire, which has been arranged in the material of the balloon. Such preferred embodiments can be effected in a relatively simple manner generally known in the art, which is advantageous for the production process.

These and various other object, advantages, and features of the invention will become apparent from the following description and claims, when considered in conjunction with the appended drawings.

BRIEF DESCRIPTION OF THE DRAWINGS

FIG. 2 shows a partial cross-section perspective view of a portion of the balloon catheter of FIG. 1;

FIGS. 3A–3C show partial cross-sectional views of the balloon of FIG. 2 in different embodiments of balloon catheters according to the present invention;

FIG. 6 shows a theoretical initial stage of tearing due to excessive pressure inside the balloon; and FIG. 7 shows a theoretical continuation of the tear shown in FIG. 6.

DETAILED DESCRIPTION OF THE PREFERRED EMBODIMENT

Figure 1:
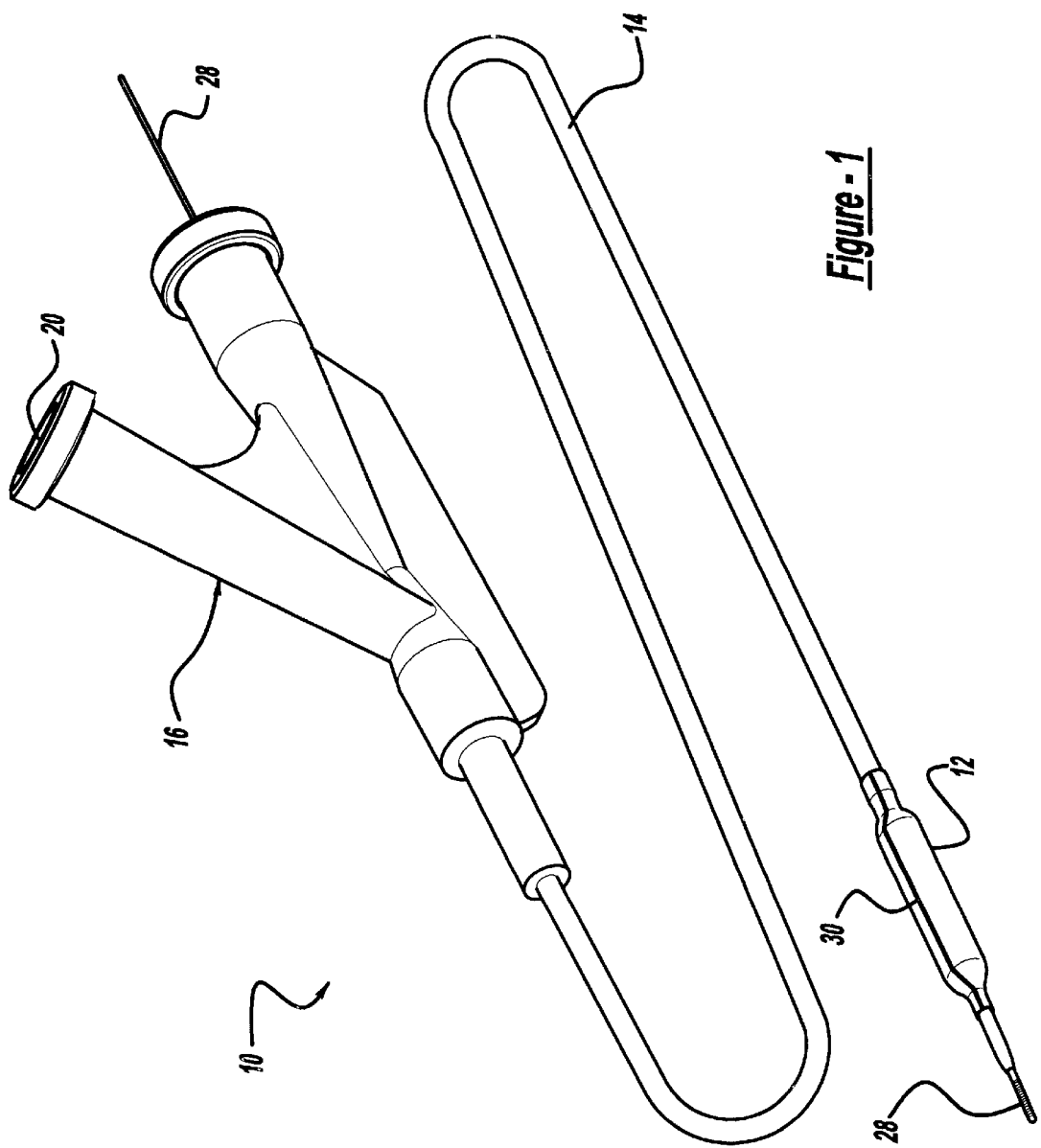
FIG. 1 is a perspective view of a balloon catheter arranged according to the principles of the present invention.

The following description of the preferred embodiments of the present invention is merely illustrative in nature, and as such it does not limit in any way the present invention, its application, or uses. Numerous modifications may be made by those skilled in the art without departing from the true spirit and scope of the invention.

Referring to the drawings, a balloon catheter is depicted, with one of the preferred embodiments of the present invention being shown generally at 10. The illustrated balloon catheter 10 of course illustrates only one of many different balloon catheter designs within the scope of the present invention.

The balloon catheter of FIG. 1 has an inflatable balloon or film material 12, a relatively long and flexible tubular shaft 14, and a hub 16. The balloon 12 is affixed to the shaft 14 near a distal end of the shaft 14, and the hub 16 is affixed to the proximal end of the shaft 14.

The shaft 14 defines one or more passages or lumens extending through the shaft, at least one of which is an inflation lumen 18 connected to the balloon 12 for the purpose of selectively inflating and deflating the balloon 12. The inflation lumen 18 thus provides fluid communication between the interior of the 12 balloon at the distal end of the inflation lumen 18, and a hub inflation port 20 having a coupling or luer-lock fitting at the proximal end for connecting the inflation lumen 18 to a source of pressurized inflation fluid (not shown) in the conventional manner.

In the illustrated embodiment, the shaft 14 is constructed of an inner and outer tubular body 22 and 24. The inner body 22 defines a guidewire lumen 26, while the inflation lumen 18 is defined by the annular space between the inner and outer tubular bodies 22 and 24. The guidewire lumen 26 is adapted to receive an elongated flexible guidewire 28 in a sliding fashion. The shaft may of course have various configurations instead of this coaxial design, including a single extruded tube defining any suitable number of parallel side-by-side lumens, a proximal shaft portion formed of a metal hypotube, and others.

The balloon 12 has been made of at least a pliable and preferably a substantially inelastic film material, in which a safety stop 30 extending in the axial direction of the balloon catheter 10 has been arranged. The possible shapes of the safety stop 30 illustrated here will be described in greater detail below with reference to the FIGS. 3A–3C.

In the balloon catheter 10 illustrated in FIG. 1, a second additional safety stop 32 has preferably been arranged at the side of the balloon 12 situated radially opposite the safety stop 30. This additional safety stop is hidden from view in the drawings by the inner tube 22.

In addition, of course of the safety stop 30 may be parallel to the longitudinal axis of the balloon catheter 10, other embodiments of the present invention (not illustrated here) are possible as well. A single safety stop or a number of safety stops may be arranged for instance in a helical pattern in the balloon 12. If selected, the helical pattern may be apparent in the deflated state of the balloon 12, but should manifest itself in the expanded state of the balloon 12.

The safety stops 30 and 32 in the balloon 12 may be made in many different ways. One possibility is to extrude the balloon parison with a stripe of polymer material having different properties. Another possible method for making the balloon of the present invention is to affix the safety stop to a balloon by any suitable method, including adhesives or heat sealing By way of addition or as an alternative, the safety stops may be provided by arranging elongated elements in the form of "stripes" embedded in the film material of which the balloon has been made. Such embodiments have been illustrated in the FIGS. 3A–3C. In FIG. 3A a strip-shaped element 34 has been arranged in the film material 12 to form the safety stop 30. The shape of the strip-shaped element 34 illustrated here is triangular, in which case the distance between the base and the top of the triangle is equal to the thickness of the film material 12. In FIG. 3B a stripe 36, arranged in the film material 12, is shown, which is rectangular in shape and also extends over the entire thickness of the film material 12. Another embodiment has been illustrated in FIG. 3C, in which case a triangular strip-shaped element 38 has been arranged in the film material to form the safety stop 30. Like in FIG. 3A, the strip-shaped element 38 is once again triangular in shape, but in this case the distance between the base and the top of the triangle is only a fraction of the thickness of the film material 12. Likewise, different arrangements or shapes may be used, including a semicircular cross-section In FIG. 4 a theoretical an initial stage of tearing of the balloon 12 has been illustrated after a puncture 40 has been formed, which may for instance have been caused by sharp points of a calcified stenosis or a sharp edge of a stent.

After the balloon 12 has been perforated by the puncture 40, the film material of the balloon 12 may tend to tear, under the influence of the pressure inside the balloon, from the site of the puncture in the direction of the safety stop 30. As soon as the tear in the balloon 12 has reached the safety stop 30, it will tend to continue along this line, thus resisting preventing a tear which runs all around the balloon in a radial direction.

The tear may tend to follow the safety stop 30 either in the proximal direction (as in the example illustrated here) or in the distal direction. Close to the proximal end of the balloon 12, the resistance of the balloon 12 to tearing increases, especially in the area where the balloon 12 has been attached to the tube 24. This is due to this attachment and to the fact that the film material, of which the balloon 12 has been made, is less expanded when located closer to the area, and therefore has a greater density and consequently a greater resistance to tearing when the tear approaches.

Figure 4:
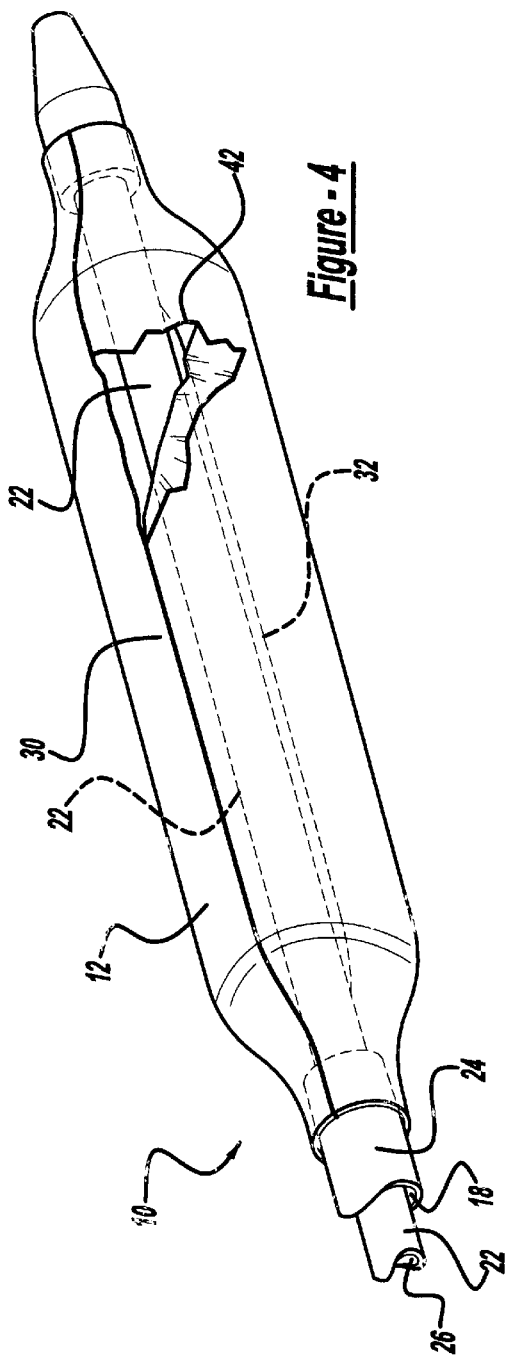
FIG. 4 shows a theoretical initial stage of tearing following puncture of a balloon from the balloon catheter of FIG. 1.
Figure 5:
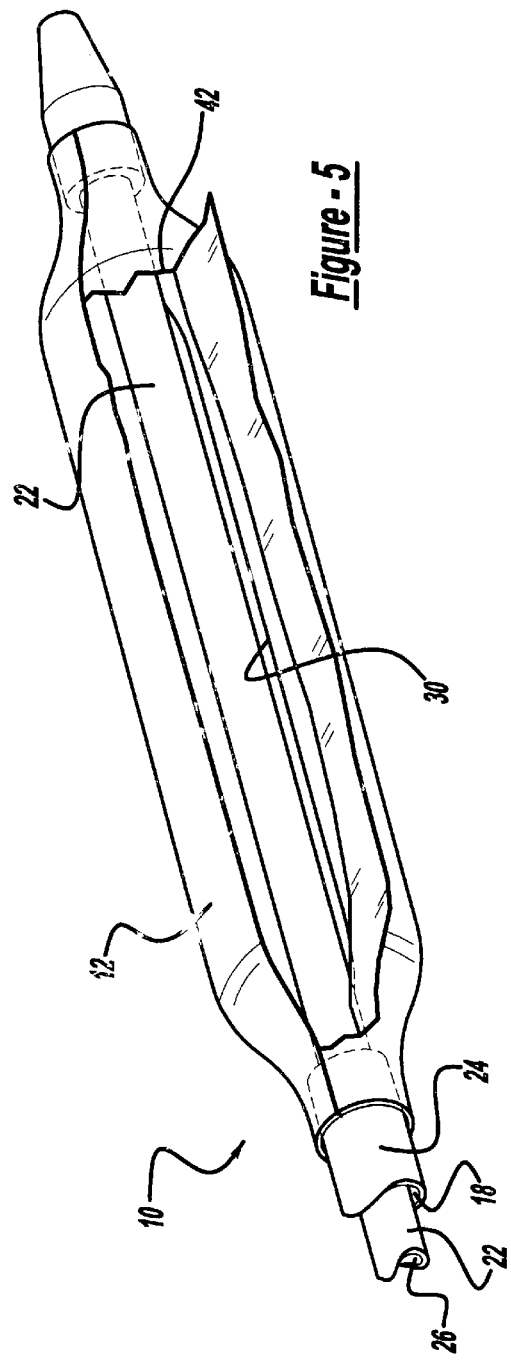
FIG. 5 shows a theoretical continuation of the tear shown in FIG. 4.
Figure 8:
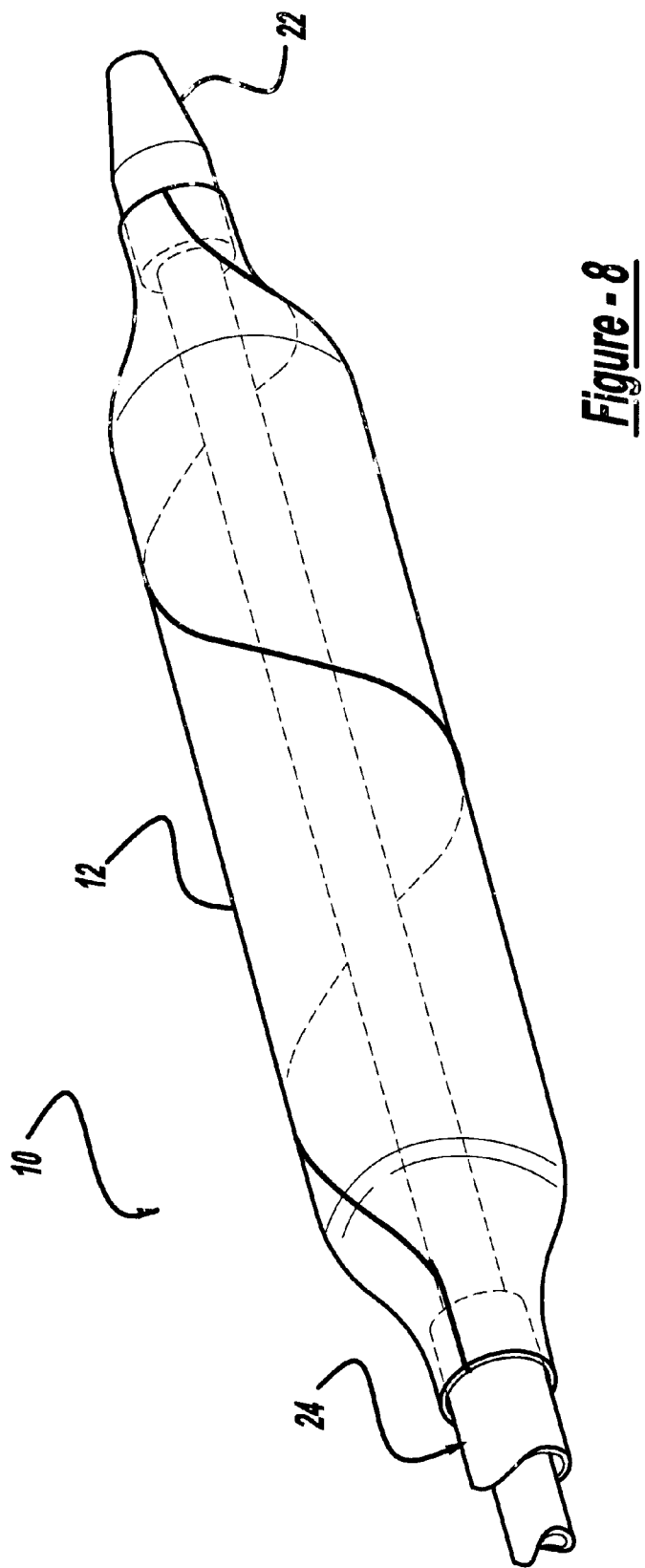
FIG. 8 shows a spiral safety stop embodiment.

In the FIGS. 4 and 5, the situation has been illustrated in which the balloon 12 bursts due to too great a pressure inside the balloon. As along the safety stop 30 the measure has consciously been taken that the strength and resistance to pressure is less here than in other sections of the balloon, a tear 42 will develop during the initial stage illustrated in FIG. 4 along the safety stop 30. As a result the pressure inside the balloon 12 will decrease.

The situation illustrated in FIG. 5, in which the tear 42 has developed along the safety stop 30, is created entirely or partially under the influence of a residual pressure inside the balloon, or because means of supplying pressure arranged at the proximal end of the balloon catheter (not illustrated here), do not stop immediately with supplying medium under pressure after the tear has been formed. Also withdrawal of the balloon catheter 10 may cause the situation illustrated in FIG. 5.

Several other embodiments of the present invention will occur to those of skill in the field after reading the description above, which should all be considered to fall within the scope of protection as defined in the attached claims, such as helically-shaped safety stops, two or more than two safety stops, etc.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed:

1. A balloon catheter for therapeutically treating a patient, comprising:

a flexible catheter shaft having proximal and distal ends, and defining at least one lumen;

a hub affixed to the shaft proximal end;

a balloon affixed to the shaft near the distal end, the balloon communicating with the lumen for selective inflation and deflation, wherein the balloon is made of a substantially inelastic material; and a safety stop affixed to the balloon and having a component extending in a longitudinal direction;

the balloon and safety stop being made of different materials having different physical properties, wherein the resulting balloon and safety stop assembly has the physical property tending to redirect a possible failure of the balloon material to follow a more longitudinal path;

wherein the safety stop is formed as a polymer insert in the wall surface of the balloon.

2. The balloon catheter as claimed in claim 1, further comprising at least one additional safety stop affixed to the balloon at a different location around the circumference of the balloon.

3. The balloon catheter as claimed in claim 1, wherein the safety stop extends in the longitudinal direction of the balloon catheter, and extends at least the full extent of a working length of the balloon.

4. The balloon catheter as claimed in the claim 1, wherein the safety stop extends in a helical pattern over the balloon in an expanded state.

5. The balloon catheter as claimed in claim 1, wherein the safety stop has a triangular wedge-shaped cross-section.

6. The balloon catheter as claimed in claim 1, wherein the safety stop has a rectangular cross-section.

7. The balloon catheter as claimed in claim 1, wherein the safety stop extends from a wall surface of the balloon material partially through the balloon wall.

8. A balloon for a balloon catheter to provide medical treatment to a patient, comprising:

a tubular substantially inelastic balloon having a central cylindrical working portion having proximal and distal ends, each end connected to a proximal and distal tapering portion respectively, and a pair of proximal and distal balloon legs connected to the tapering portions; and a safety stop affixed to the balloon and extending along at least the working portion of the balloon;

the balloon and safety stop being made of different materials having different physical properties, wherein the resulting balloon and safety stop assembly has the physical property tending to redirect a possible failure of the balloon material to follow a more longitudinal path;

wherein the safety stop is formed as a polymer insert in the wall surface of the balloon.

* * * * *

UNITED STATES PATENT AND TRADEMARK OFFICE
CERTIFICATE OF CORRECTION

| | | |
|---|---|---|
| PATENT NO. | : 6,355,013 B1 | |
| APPLICATION NO. | : 09/594854 | |
| DATED | : March 12, 2002 | |
| INVENTOR(S) | : Johannes G. M. van Muiden | |

It is certified that error appears in the above-identified patent and that said Letters Patent is hereby corrected as shown below:

Figure 5 drawing number 30 should read 32

Figure 6 drawing number 30 should read 32

Figure 7 drawing number 30 should read 32

Signed and Sealed this

First Day of May, 2007

JON W. DUDAS
*Director of the United States Patent and Trademark Office*